US012214024B2

(12) United States Patent
Xue et al.

(10) Patent No.: US 12,214,024 B2
(45) Date of Patent: Feb. 4, 2025

(54) USE OF APC ANALOGUE FOR WOUND HEALING

(71) Applicant: ZZ Biotech LLC, Houston, TX (US)

(72) Inventors: Meilang Xue, New South Wales (AU); Christopher John Jackson, New South Wales (AU)

(73) Assignee: ZZ Biotech LLC, Houston, TX (US)

( * ) Notice: Subject to any disclaimer, the term of this patent is extended or adjusted under 35 U.S.C. 154(b) by 483 days.

(21) Appl. No.: 16/569,975

(22) Filed: Sep. 13, 2019

(65) Prior Publication Data

US 2020/0000890 A1     Jan. 2, 2020

Related U.S. Application Data

(63) Continuation of application No. 15/897,801, filed on Feb. 15, 2018, now abandoned, which is a continuation of application No. 15/304,433, filed as application No. PCT/AU2015/050177 on Apr. 16, 2015, now abandoned.

(30) Foreign Application Priority Data

Apr. 16, 2014 (AU) .................................. 2014901397
Jul. 25, 2014 (AU) .................................. 2014902900

(51) Int. Cl.
*A61K 38/48*    (2006.01)
*A61K 9/00*    (2006.01)
*A61L 26/00*    (2006.01)

(52) U.S. Cl.
CPC ........ *A61K 38/4866* (2013.01); *A61K 9/0014* (2013.01); *A61K 9/0019* (2013.01); *A61L 26/0066* (2013.01); *A61L 26/0076* (2013.01); *A61L 26/008* (2013.01); *A61L 2300/252* (2013.01); *C12Y 304/21069* (2013.01)

(58) Field of Classification Search
None
See application file for complete search history.

(56) References Cited

U.S. PATENT DOCUMENTS

| 4,775,624 A | 10/1988 | Bang et al. |
| 4,959,318 A | 9/1990 | Foster et al. |
| 4,981,952 A | 1/1991 | Yan |

(Continued)

FOREIGN PATENT DOCUMENTS

| AU | 658881 | 11/1992 |
| CA | 2041380 C | 10/1997 |

(Continued)

OTHER PUBLICATIONS

Boulaftali et al, Endothelial Protease Nexin-1 Is a Novel Regulator of A Disintegrin and Metalloproteinase 17 Maturation and Endothelial Protein C Receptor Shedding via Furin Inhibition, 2013, Arterioscler Thromb Vasc Biol., 33:1647-1654 (Year: 2013).*

(Continued)

*Primary Examiner* — Sharmila G Landau
*Assistant Examiner* — Stephanie A McNeil
(74) *Attorney, Agent, or Firm* — Myers Bigel, P.A.

(57) ABSTRACT

The invention relates to wound repair and healing, particularly to dermal or cutaneous wounds including but not limited to acute and chronic wounds, burns and ulcers.

17 Claims, 6 Drawing Sheets

Specification includes a Sequence Listing.

(56) References Cited

U.S. PATENT DOCUMENTS

| | | | |
|---|---|---|---|
| 5,084,274 | A | 1/1992 | Griffin et al. |
| 5,093,117 | A | 3/1992 | Lawrence et al. |
| 5,151,268 | A | 9/1992 | Bang et al. |
| 5,453,373 | A | 9/1995 | Gerlitz et al. |
| 5,516,650 | A | 5/1996 | Foster et al. |
| 5,571,786 | A | 11/1996 | Eibl et al. |
| 5,726,205 | A | 3/1998 | Woitun et al. |
| 5,831,025 | A | 11/1998 | Ogata et al. |
| 6,037,322 | A | 3/2000 | Grinnell et al. |
| 6,156,734 | A | 12/2000 | Grinnell et al. |
| 6,159,468 | A | 12/2000 | Carlson et al. |
| 6,268,344 | B1 | 7/2001 | Grinnell et al. |
| 6,395,270 | B1 | 5/2002 | Carlson et al. |
| 2004/0176288 | A1 | 9/2004 | Jackson et al. |
| 2007/0224150 | A1 | 9/2007 | Chung |
| 2011/0129546 | A1 | 6/2011 | Umbert Mill |
| 2013/0280234 | A1 | 10/2013 | Jackson et al. |

FOREIGN PATENT DOCUMENTS

| | | |
|---|---|---|
| CN | 101912450 A | 12/2010 |
| EP | 2 157 176 A1 | 2/2010 |
| WO | WO 89/012685 A1 | 12/1989 |
| WO | WO 93/09807 A1 | 5/1993 |
| WO | WO 95/29148 A1 | 11/1995 |
| WO | WO 95/30429 A1 | 11/1995 |
| WO | WO 98/48818 A1 | 11/1998 |
| WO | WO 01/56532 A2 | 8/2001 |
| WO | WO 01/59084 A1 | 8/2001 |
| WO | WO 01/72328 A1 | 10/2001 |
| WO | WO 02/32461 A2 | 4/2002 |
| WO | WO 02/100445 A1 | 12/2002 |
| WO | WO 2004/041296 A2 | 5/2004 |
| WO | 2004096216 | 11/2004 |
| WO | WO 2005/007820 A2 | 1/2005 |
| WO | 2006136963 A2 | 12/2006 |
| WO | WO 2008/026014 A1 | 3/2008 |
| WO | WO 2008/055145 A2 | 5/2008 |
| WO | WO 2008/073603 A2 | 6/2008 |
| WO | 2009074797 A1 | 6/2009 |
| WO | WO 2014/005183 A1 | 1/2014 |
| WO | WO 2015/157791 A1 | 10/2015 |

OTHER PUBLICATIONS

Freedberg et al. "Keratins and the Keratinocyte Activation Cycle" The Journal of Investigative Dermatology, 116(5):633-640 (2001).
Fukushiro, Torii "Characteristics of cultured cells of human epidermal keratinocytes from hypertrophic scars and of its apoptosis" Proceedings from the 13th Conference on Disorders of Keratinisation (12 pages) (1999).
Mosnier et al. "Activated protein C variants with normal cytoprotective but reduced anticoagulant activity" Blood, 104(6):1740-1744 (2004).
Abdou et al. "Immunohistochemical Expression of TGF-β1 in Keloids and Hypertrophic Scars" *American Journal of Dermatopathology* 33(1):84-91 (2011).
Al-Khawajah, Marwan M. "Failure of Interferon-Alpha 2B in the Treatment of Mature Keloids" *International Journal of Dermatology* 35(7):515-517 (1996).
Altschul et al. "Gapped BLAST and PSI-BLAST: a new generation of protein database search programs" *Nucleic Acids Research* 25(17):3389-3402 (1997).
Berth-Jones et al. "Vitamin D analogues and psoriasis" *British Journal of Dermatology* 127:71-78 (1992).
Bettinger et al. "The Effect of TGF-β on Keloid Fibroblast Proliferation and Collagen Synthesis" *Plastic and Reconstructive Surgery* 98(5):827-833 (1996).
Bush et al. "Therapies with Emerging Evidence of Efficacy: Avotermin for the Improvement of Scarring" *Dermatology and Research Practice* 2010:1-6 (2010).

Chiricozzi et al. "Integrative Responses to IL-17 and TNF-α in Human Keratinocytes Account for Key Inflammatory Pathogenic Circuits in Psoriasis" *Journal of Investigative Dermatology* 131:677-687 (2011).
Chalmers, Richard L "The evidence for the role of transforming growth factor-beta in the formation of abnormal scarring" *International Wound Journal* 8:218-223 (2011).
Cordeiro et al. "Novel antisense oligonucleotides targeting TGF-β inhibit in vivo scarring and improve surgical outcome" *Gene Therapy* 10:59-71 (2003).
Esmon, Charles T. "Structure and functions of the endothelial cell protein C receptor" *Critical Care Medicine* 32[Suppl.]:S298-S301 (2004).
Esmon, Charles T. "Crosstalk between inflammation and thrombosis" *Maturitas* 47:305-314 (2004).
Feistritzer et al. "Endothelial barrier protection by activated protein C through PAR1-dependent sphingosine 1-phosphate receptor-1 crossactivation" *Blood* 105:3178-3184 (2005).
Ferguson et al. "Scar-free healing: from embryonic mechanisms to adult therapeutic intervention" *Philosophical Transactions of the Royal Society B: Biological Sciences* 359(1445):839-850 (2004).
Finigan et al. "Activated Protein C Mediates Novel Lung Endothelial Barrier Enhancement" *The Journal of Biological Chemistry* 280(17):17286-17293 (2005).
Guo et al. "Neuroprotective activities of activated protein C mutant with reduced anticoagulant activity" *European Journal of Neuroscience* 29:1119-1130 (2009).
Herrier, RN "Advances in the treatment of moderate-to-severe plaque psoriasis" *American Journal of Health-System Pharmacy* 68(9):795-806 (2011) (Abstract Only).
Honardoust et al. "Reduced Decorin, Fibromodulin, and Transforming Growth Factor-β3 in Deep Dermis Leads to Hypertrophic Scarring" *Journal of Burn Care & Research* 33(2):218-227 (2012).
International Search Report and the Written Opinion of the International Searching Authority corresponding to International Patent Application No. PCT/AU2015/050177 (9 pages) (mailed Jun. 16, 2015).
Jackson et al. "Activated protein C prevents inflammation yet stimulates angiogenesis to promote cutaneous wound healing" *Wound Repair and Regeneration* 13(3):284-294 (2005).
Kerschen et al. "Endotoxemia and sepsis mortality reduction by non-anticoagulant-activated protein C" *The Journal of Experimental Medicine* 204(10):2439-2448 (2007).
Kurian et al. "Current Effective Topical Therapies in the Management of Psoriasis" *Skin Therapy Letter* 16(1):4-7 (2011).
Kur-Piotrowska et al. "Neotenic phenomenon in gene expression in the skin of Foxn1-deficient (nude) mice—a projection for regenerative skin wound healing" *BMC Genomics* 18(56):1-15 (2017).
Lay et al. "Acute inflammation is exacerbated in mice genetically predisposed to a severe protein C deficiency" *Blood* 109:1984-1991 (2007).
Le et al. "Transforming Growth Factor Beta 3 Is Required for Excisional Wound Repair In Vivo" *PLoS One* 7(10):1-10 (2012).
Ledon et al. "Intralesional Treatment for Keloids and Hypertrophic Scars: A Review" *Dermatologic Surgery* 39:1745-1757 (2013).
Lee et al. "Expression of Transforming Growth Factor Beta 1, 2, and 3 Proteins in Keloids" *Annals of Plastic Surgery* 43(2):179-184 (1999).
Lin et al. "Exogenous Transforming Growth Factor-Beta Amplifies Its Own Expression and Induces Scar Formation in a Model of Human Fetal Skin Repair" *Annals of Plastic Surgery* 222(2):146-154 (1995).
Machesney et al. "Activated Keratinocytes in the Epidermis of Hypertrophic Scars" *American Journal of Pathology* 152(5):1133-1141 (1998).
Matsumoto et al. "Activated protein C modulates the proinflammatory activity of dendritic cells" *Journal of Asthma and Allergy* 8:29-37 (2015).
McCollum et al. "Randomized Phase II clinical trial of avotermin versus placebo for scar improvement" *The British Journal of Surgery* 98(7):925-934 (2011).

(56) References Cited

OTHER PUBLICATIONS

McCoy et al. "In Vitro Inhibition of Cell Growth, Collagen Synthesis, and Prolyl Hydroxylase Activity by Triamcinolone Acetonide" *Proceedings of the Society for Experimental Biology and Medicine* 163(2):216-222 (1980).

McKelvey et al. "Activated protein C: A regulator of human skin epidermal keratinocyte function" *World Journal of Biological Chemistry* 5(2):169-179 (2014).

Momtazi et al. "A nude mouse model of hypertrophic scar shows morphologic and histologic characteristics of human hypertrophic scar" *Wound Repair and Regeneration* 21(1):77-87 (2013).

Montesu et al. "Adverse reactions during biological drug therapy in psoriasis: clinical series and a review of the literature" *G. Ital. Dermatol. Venereol.* 146(4):273-281 (2011) (Abstract Only).

Mosnier et al. "Protein C anticoagulant activity in relation to anti-inflammatory and anti-apoptotic activities" *Frontiers in Bioscience* 11:2381-2399 (2006).

Nestle et al. "Skin immune sentinels in health and disease" *Nature Reviews Immunology* 9(10):679-691 (2009).

Occleston et al. "Prevention and reduction of scarring in the skin by Transforming Growth Factor beta 3 (TGFB3): from laboratory discovery to clinical pharmaceutical" *Journal of Biomaterials Science, Polymer Edition* 19(8):1047-1063 (2008).

Office Action corresponding to Russian Patent Application No. 2015103510 (12 pages) (dated Dec. 8, 2017).

O'Brien et al. "Activated Protein C Decreases Tumor Necrosis Factor-Related Apoptosis-Inducing Ligand by an EPCR-Independent Mechanism Involving Egr-1/Erk-1/2 Activation" *Arteriosclerosis, Thrombosis, and Vascular Biology* 27(12):2634-2641 (2007).

Pasparakis, Manolis "Regulation of tissue homeostasis by NF-κB signalling: implications for inflammatory diseases" *Nature Reviews Immunology* 9:778-788 (2009).

Pasparakis, Manolis "Role of NF-κB in epithelial biology" *Immunological Reviews* 246:346-358 (2012).

Pearson, William R. "Searching Protein Sequence Libraries: Comparison of the Sensitivity and Selectivity of the Smith-Waterman and FASTA Algorithms" *Genomics* 11(3):635-650 (1991).

Profyris et al. "Cutaneous scarring: Pathophysiology, molecular mechanisms, and scar reduction therapeutics Part I. The molecular basis of scar formation" *Journal of the American Academy of Dermatology* 66(1):1-10 (2012).

Shah et al. "Neutralising antibody to TGF-$\beta_{1,2}$ reduces cutaneous scarring in adult rodents" *Journal of Cell Science* 107:1137-1157 (1994).

Skripin, Y.K. "Skin and Venereal Diseases" M, Triada-X, p. 363 (2000).

Smith et al. "Identification of Common Molecular Subsequences" *Journal of Molecular Biology* 147(1):195-197 (1981).

Thompson et al. "Genetic Risk Factors for Hypertrophic Scar Development" *Journal of Burn Care & Research* 34(5):477-482 (2013).

Tran et al. "Insight into psoriasis management: Commercial perspectives for the U.S. psoriasis market" *Journal of Dermatological Treatment* 22:18-26 (2011).

Uchiba et al. "Activated Protein C Induces Endothelial Cell Proliferation by Mitogen-Activated Protein Kinase Activation In Vitro and Angiogenesis In Vivo" *Circulation Research* 95:34-41 (2004).

Van Zonneveld et al. "Inflammation, vascular injury and repair in rheumatoid arthritis" *Annals of the Rheumatic Diseases* 69(Suppl. 1):i57-i60 (2010).

Vetrano et al. "Unexpected role of anticoagulant protein C in controlling epithelial barrier integrity and intestinal inflammation" *Proceedings of the National Academy of Sciences* 108(49):19830-19835 (2011).

Walker et al. "Activated protein C analog with reduced anticoagulant activity improves functional recovery and reduces bleeding risk following controlled cortical impact" *Brain Research* 1347:125-131 (2010).

Wallis, Robert S. "Biologics and Infections: Lessons from Tumor Necrosis Factor Blocking Agents" *Infectious Disease Clinics of North America* 25(4):895-910 (2011).

Wang et al. "An Activated Protein C Analog With Reduced Anticoagulant Activity Extends the Therapeutic Window of Tissue Plasminogen Activator for Ischemic Stroke in Rodents" *Stroke* 43(9):2444-2449 (2012).

White et al. "Activated protein C inhibits lipopolysaccharide-induced nuclear translocation of nuclear factor κB (NF-κB) and tumour necrosis factor α (TNF-α) production in the THP-1 monocytic cell line" *British Journal of Haematology* 110:130-134 (2000).

Williams et al. "Preclinical Safety and Pharmacokinetic Profile of 3K3A-APC, a Novel, Modified Activated Protein C for Ischemic Stroke" *Current Pharmaceutical Design* 18(27):4215-4222 (2012).

Xia et al. "Complex epithelial-mesenchymal interactions modulate transforming growth factor-β expression in keloid-derived cells" *Wound Repair and Regeneration* 12(5):546-556 (2004).

Xue et al. "Activated protein C stimulates proliferation, migration and wound closure, inhibits apoptosis and upregulates MMP-2 activity in cultured human Keratinocytes" *Experimental Cell Research* 299:119-127 (2004).

Xue et al. "Endothelial Protein C Receptor and Protease-Activated Receptor-1 Mediate Induction of a Wound-Healing Phenotype in Human Keratinocytes by Activated Protein C" *Journal of Investigative Dermatology* 125:1279-1285 (2005).

Xue et al. "Endothelial protein C receptor is Overexpressed in rheumatoid arthritic (RA) synovium and mediates the anti-inflammatory effects of activated protein C in RA monocytes" *Annals of the Rheumatic Diseases* 66:1574-1580 (2007).

Xue et al. "Differential Regulation of Matrix Metalloproteinase 2 and Matrix Metalloproteinase 9 by Activated Protein C" *Arthritis & Rheumatism* 56(9):2864-2874 (2007).

Xue et al. "Protein C Is an Autocrine Growth Factor for Human Skin Keratinocytes" *The Journal of Biological Chemistry* 282(18):13610-13616 (2007).

Xu et al. "Comparison of the mechanisms of intralesional steroid, interferon or verapamil injection in the treatment of proliferative scars" Zhonghua zhengxing waike zazhi 25(1):37-40 (2009) (Abstract Only).

Yuksel et al. "Activated Protein C Inhibits Lipopolysaccharide-Induced Tumor Necrosis Factor-α Production by Inhibiting Activation of both Nuclear Factor-κB and Activator Protein-1 in Human Monocytes" *Thrombosis and Haemostasis* 88:267-273 (2002).

Zaba et al. "Identification of TNF-related apoptosis-inducing ligand and other molecules that distinguish inflammatory from resident dendritic cells in patients with psoriasis" *Journal of Allergy and Clinical Immunology* 125(6):1261-1268 (2010).

Zanni, Guido "Psoriasis: issues far more serious than cosmetic" *The Consultant Pharmacist* 27(2):86-88, 90, 93-86 (2012) (Abstract Only).

Guo, Huang, et al., "An Activated Protein C Analog Stimulates Neuronal Production by Human Neural Progenitor Cells via a PAR1-PAR3-S1PR1-Akt Pathway", The Journal of Neuroscience, 33(14):6181-6190 (2013).

Julovi, Sohel M., et al., "Protease Activated Receptor-2 Mediates Activated Protein C-Induced Cutaneous Wound Healing via Inhibition of p38", The American Journal of Pathology, 179(5):2233-2242 (2011).

Xue, et al., "Activated Protein C Enhances Human Keratinocyte Barrier Integrity via Sequential Activation of Epidermal Growth Factor Receptor and Tie2" The Journal of Biological Chemistry 286(8):6742-6750 (2011).

Andriessen et al. "Hypertrophic scarring is associated with epidermal abnormalities: an immunohistochemical study" Journal of Pathology, 186:192-200 (1998).

Bae et al. "Thrombin Down-Regulates the TGF-β-Mediated Synthesis of Collagen and Fibronectin by Human Proximal Tubule Epithelial Cells Through the EPCR-Dependent Activation of PAR-1" Journal of Cellular Physiology, 225:233-239 (2010).

English Translation of Office Action corresponding to Chinese Patent Application No. 201480078924.1 (11 pages) (dated Oct. 8, 2019).

(56) References Cited

OTHER PUBLICATIONS

Jiang et al. "Epidermal growth factor and transforming growth factor alpha specifically induce the activation- and hyperproliferation-associated keratins 6 and 16" Proceedings of the National Academy of Sciences USA, 90:6786-6790 (1993).

Herdrich et al. "Fetal Tendon Wound Size Modulates Wound Gene Expression and Subsequent Wound Phenotype" Wound Repair and Regeneration, 18:543-549 (2010).

Cabrijan et al. "Psoriasis Vulgaris—An Inflammatory Skin Disease and/or Benign Epidermal Hyperplasia" Acta Dermatovenerologica Croatica 19(2):117-119 (2011).

Kuroda et al. "Altered Expression of Angiopoietins and Tie2 Endothelium Receptor in Psoriasis" Journal of Investigative Dermatology 116:713-720 (2001).

Mosnier et al. "The cytoprotective protein C pathway," Blood, Apr. 15, 2007; 109(8):3161-72.

\* cited by examiner

Figure 6

ANSFLEELRHSSLERECIEEICDFEEAKEIFQNVDDTLAFWSKHVDGDQCLVLPLEHPCAS
LCCGHGTCIDGIGSFSCDCRSGWEGRFCQREVSFLNCSLDNGGCTHYCLEEVGWRRCS
CAPGYKLGDDLLQCHPAVKFPCGRPWKRMEKKRSHLKRDTEDQEDQVDPRLIDGKMTR
RGDSPWQVVLLDSAAALACGAVLIHPSWVLTAAHCMDESKKLLVRLGEYDLRRWEKWEL
DLDIKEVFVHPNYSKSTTDNDIALLHLAQPATLSQTIVPICLPDSGLAERELNQAGQETLVT
GWGYHSSREKEAKRNRTFVLNFIKIPVVPHNECSEVMSNMVSENMLCAGILGDRQDACE
GDSGGPMVASFHGTWFLVGLVSWGEGCGLLHNYGVYTKVSRYLDWIHGHIRDKEAPQK
SWAP

USE OF APC ANALOGUE FOR WOUND HEALING

CROSS REFERENCE TO RELATED APPLICATIONS

This application is a continuation of U.S. application Ser. No. 15/897,801, filed Feb. 15, 2018, which is a continuation of U.S. application Ser. No. 15/304,433, filed Oct. 14, 2016, which is a filing under 35 U.S.C. 371 of PCT/AU2015/050177, filed Apr. 16, 2015, which claims priority from Australian Patent Application No. 2014902900, filed Jul. 25, 2014, and Australian Patent Application No. 2014901397, filed Apr. 16, 2014. These prior applications are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9975-9CT2_ST25.txt, 4,125 bytes in size, generated on Sep. 12, 2019 and filed via EFS-Web, is provided in lieu of a paper copy. This Sequence Listing is hereby incorporated by reference into the specification for its disclosures.

FIELD OF THE INVENTION

The invention relates to wound repair and healing, particularly to dermal or cutaneous wounds including but not limited to acute and chronic wounds, burns and ulcers.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

In the adult, the normal response to injury is generally wound repair. Wound repair has been classically described as following three distinct phases consisting of an initial phase in which a fibrin clot is formed, an intermediate phase in which the fibrin clot is lysed and a temporary matrix consisting of proteoglycan, glycoprotein and type III collagen is laid down, and a final phase in which the temporary phase is digested and replaced with a matrix rich in collagen type I.

Local factors such as the type, size and location of the wound, the vascular supply to the wound, the presence of infection, local movement, and exposure to radiation and UV light influence wound repair, as do systemic factors including status of cardiovascular performance, infection, metabolic status and hormones.

It is generally accepted that a normal physiological response to injury is a wound repair process that is complete with evidence of collagen type I deposition by about 3 to 4 weeks from injury. A protraction of the wound repair process beyond this time increases the likelihood of formation of a chronic wound.

While the role of inflammation in wound healing is under debate, it is generally recognised that it is important to contain inflammation during wound healing in terms of the severity and duration of inflammation. In particular it has been observed that an absence of inflammation in wound healing is linked with regeneration, whereas presence of inflammation results in some degree of fibrosis and scar formation. Further, extended inflammation can lead to chronic inflammation, and insofar as cutaneous wounds are concerned, a failure for a wound to properly close, and ulceration.

Topical application of activated protein C (APC) has been shown to provide improvements in cutaneous wounds including dermal ulcers, burns, oral wounds, bone and cartilage damage, eye wounds and warfarin-related skin necrosis. According to WO2002/100445, it is the anti-coagulation and anti-inflammatory functions of APC that strongly indicate that APC is useful for the treatment of dermal wounds, and in particular for treatment of slow healing wounds. WO2002/100445 also discusses that APC-mediated gelatinase A-activating functions are important for APC-mediated wound repair.

Further to anti-coagulation and anti-inflammatory functions, APC is also known to have an anti-apoptotic function. The anti-apoptotic function is known to be independent of the anti-coagulation function, and in particular it is known that at least 3 lysine residues on the 37-loop of APC are essential for APC-mediated cleavage of factor Va, whereas these residues are not required for the anti-apoptotic, cyto-protective activity that arises by APC-mediated activation of PAR-1 Mosnier and Griffin 2006 Frontiers in Bioscience 11 2381-2399.

While the anti-inflammatory function of APC is thought to arise from APC-mediated activation of at least EPCR and possibly PAR-1, possibly leading to reduced leukocyte activation, dampened release of inflammatory cytokines, reduced extravasation of inflammatory cells at inflammatory sites, the mechanism(s) of the APC-mediated interaction(s), and in particular the relevant conformation site(s) of APC required for the anti-inflammatory function are not known. Mosnier supra. Further to APC-receptor mediated interactions, it has also been thought that APC's anti-inflammatory activity could well be explained by reason of its ability to down regulate generation of the proteases of the coagulation pathway, potentially linking anti-inflammatory activity and anti-coagulation activity.

APC-3K3A is an analogue of APC in which the 3 lysine residues on the 37-loop of APC relevant for Factor Va cleavage have been removed, enabling the analogue to provide anti-apoptotic function whilst eliminating anti-coagulation function. This analogue was prepared for the sole purpose of providing full cyto-protective activity in conditions involving apoptosis (including stroke and neurodegenerative disorders) while reducing risk of bleeding. Mosnier supra.

There remains a need for improvements in dermal wound repair, in particular for improving the time to wound repair, for improving the rate of wound repair in particular by accelerating wound repair, or for improving the quality of a tissue arising from wound repair.

SUMMARY OF THE INVENTION

The invention seeks to address one or more of the above mentioned needs and in one embodiment provides a method for the treatment of a dermal wound including the step of contacting a dermal wound with an effective amount of APC-3K3A, thereby treating the dermal wound.

In another embodiment there is provided a method of decreasing the wound area or volume of a dermal wound including the step of contacting a dermal wound with an effective amount of APC-3K3A, thereby decreasing the wound area or volume of the dermal wound.

In another embodiment there is provided a method of accelerating the rate of wound healing, or decreasing the time to completion of wound healing or wound closure including the step of contacting a dermal wound with an effective amount of APC-3K3A, thereby accelerating the rate of wound healing, or decreasing the time to completion of wound healing or wound closure.

In another embodiment there is provided a method of accelerating the rate of wound healing during the first 3 to 7 days, preferably the first 3 to 5 days, preferably the first 3 days following wound formation, including the step of contacting a dermal wound after wound formation with an effective amount of APC-3K3A, thereby accelerating the rate of wound healing. The effective amount of APC-3K3A may be contacted with the dermal wound within 48 hours, preferably within 24 hours or within 12 hours from wound formation. Typically the rate of wound healing is accelerated relative to an untreated wound, or relative to a wound which has been treated with an equivalent amount of APC.

In another embodiment there is provided a method of inducing or promoting or initiating a wound repair mechanism in a dermal wound including the step of contacting a dermal wound with an effective amount of APC-3K3A, thereby inducing or promoting or initiating a wound repair mechanism in a dermal wound. In this embodiment, the wound may be a chronic wound which is devoid of, or which has minimal active wound repair mechanisms.

In another embodiment there is provided a method of minimising inflammation associated with wound repair including the step contacting a dermal wound with an effective amount of APC-3K3A, thereby minimising inflammation associated with wound repair.

In another embodiment there is provided a use of APC-3K3A in the manufacture of a medicament for treating a dermal wound.

In another embodiment there is provided use of APC-3K3A for treating a dermal wound.

In another embodiment there is provided APC-3K3A or formulation containing same including an effective amount of APC-3K3A for use in treatment of a dermal wound.

In the above described embodiments the wound is typically not associated with significant apoptosis. Typically, the dermal wound is not characterised by significant apoptosis, or otherwise does not arise from apoptosis In the above described embodiments, the effective amount of APC-3K3A may be topically administered to the wound thereby contacting the wound with the APC-3K3A.

In another embodiment there is provided a formulation for treatment of a dermal wound, wherein the formulation includes APC-3K3A. In this embodiment, the formulation is adapted for topical application to a dermal wound. The formulation may be in the form of a gel, ointment, lotion or spray.

In another embodiment there is provided a device, personal care article or dressing formulated or adapted for treatment or management of a dermal wound including an effective amount of APC-3K3A for treatment or management of a dermal wound. In this embodiment the APC-3K3A may be provided in the form of a gauze, mesh, sponge or bandage.

In the above described embodiments, the dermal wound may be chronic or acute wound and may arise from laceration, burn, incision, maceration, crushing, puncture abrasion or like injury.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 6. Amino acid sequence (SEQ ID NO:1) of APC-3K3A.

DETAILED DESCRIPTION OF THE EMBODIMENTS

Figure 1:
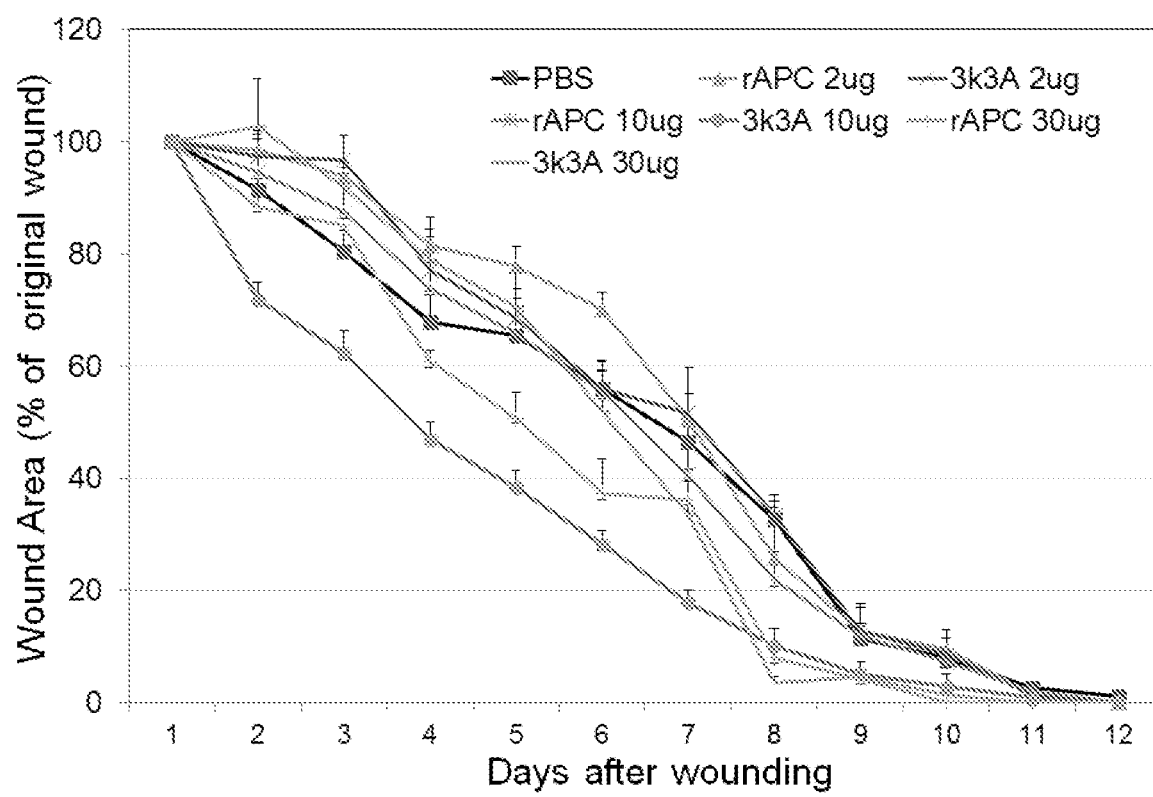
FIG. 1. Decreases in wound area as a percentage of original wound in APC, APC-3K3A treated mice.

It will be understood that the invention disclosed and defined in this specification extends to all alternative combinations of two or more of the individual features mentioned or evident from the text or drawings. All of these different combinations constitute various alternative aspects of the invention.

As discussed above, APC-3K3A is an analogue of APC in which the 3 lysine residues on the 37-loop of APC relevant for Factor Va cleavage have been removed, enabling the analogue to provide anti-apoptotic function whilst eliminating anti-coagulation function. The sequence of APC-3K3A is shown in FIG. 6.

APC-3K3A was prepared for the sole purpose of providing full cyto-protective activity in conditions involving apoptosis (including stroke and neurodegenerative disorders) while reducing risk of bleeding. Mosnier supra. According to WO2005/007820, APC-3K3A is designed to enable it to be used for preventing or alleviating damage associated at least in part with apoptosis including in subjects at risk of damage to blood vessels or tissue in various organs caused at least in part by apoptosis. See also WO2008/055145; WO2008/073603; Wang et al. 2012 Stroke 43:2444-2449; and Guo et al. 2009 Eur. J. Neurosci. 29:1119-1130.

The inventors have found that APC-3K3A can be used to improve dermal wound repair. The finding is particularly surprising given that apoptosis is not generally considered to be a cell mechanism that underpins repair of dermal wounds or that is involved in wound pathology including formation of a chronic wound.

This finding has been made in circumstances where prior to the invention, at least the anti-coagulant activity of APC was understood to be relevant to dermal wound repair, and there was a paucity of knowledge regarding whether the elimination of anti-coagulation function would impact on the Gelatinase A activity and anti-inflammatory function of APC necessary for repair of a dermal wound.

One particularly surprising finding of the invention is that APC-3K3A can be utilised to provide a dermal wound repair response that is improved over that observed with APC anti-coagulant function. Specifically, as shown in the examples herein, the inventors have found that APC-3K3A can be used to accelerate wound healing rate and to reduce the time to wound healing in in vivo excision models. Thus in one embodiment there is provided a method for the treatment of a dermal wound including the step of contacting a dermal wound with an effective amount of APC-3K3A, thereby treating the dermal wound.

In the above described method, the individual may be one at risk for impaired wound repair or impaired wound healing. In particular, the individual may be one having systemic or local risk factors for protracted wound repair. Systemic risk factors include systemic infection, metabolic syndrome, diabetes or glucose intolerance, impaired cardiovascular function. Local risk factors include those pertaining to the injury including the nature of the injury itself (for example, a trauma or burn), abnormal inflammation, repeated physical stress by movement, or exposure to UV radiation.

The invention may include the step of assessing an individual to determine whether the individual or injury site has one or more systemic or local risk factors described above for an impaired wound repair process. Typically, the individual is assessed for one or more systemic or local risk factors applicable to formation of a chronic wound such as those described herein.

Where the individual is assessed as having one or more local or systemic risk factors for an impaired wound repair process, the method may include the further step of selecting the individual for treatment with APC-3K3A to minimise the likelihood of onset of an impaired wound repair process.

Typically the injury is one arising from insult to dermal, cutaneous or skin tissue. The insult may impact on all layers of dermal tissue, for example on stratum basale (stratum germinativum), stratum *spinosum*, stratum *granulosum*, stratum lucidum. Examples of particular injury include laceration, abrasion, rupture, burn, contusion, compression.

The injury may be a burn, including a 1st, 2nd or 3rd degree burn.

Typically the injury is an acute injury.

In one embodiment, the injury may not be associated with chronic inflammation.

Typically the injury is not associated with fibrosis.

Typically the injury is not an inflammatory disorder, an allergic disorder, or an idiopathic disorder or disease.

The APC-3K3A may be applied to the site of tissue injury before the wound repair process has formed a fibrin clot. In another embodiment the APC-3K3A may be applied to the site of tissue injury before the wound repair process has formed a temporary matrix. In another embodiment the APC-3K3A may be applied to the site of tissue injury before the wound repair process has formed a final matrix. Typically the APC-3K3A is applied at about the time of, or shortly after, formation of the temporary matrix.

Typically the individual is treated with APC-3K3A so as to provide for completion of wound repair within about 3 to 4 weeks of tissue injury.

Notwithstanding the foregoing, it is understood by those skilled in the art that the dosage amount of the APC-3K3A will vary with the disease or condition to be treated, the severity of the disease or condition, the type(s) of local administration, the rate of excretion of the compound, the duration of the treatment, the identify of any other drugs being administered to the animal, the age, size and species of the animal, and like factors known in the medical arts. In general, a suitable daily dose of a compound or combination of compounds will be that amount which is the lowest dose effective to produce a therapeutic effect. The dosage amount, dosage form and mode of administration will be determined by an attending physician within the scope of sound medical judgment. Effective dosage amounts, dosage forms, and modes of administration for the various compounds and combination(s) of compounds can be determined empirically and making such determinations is within the skill of the art.

In certain embodiments, it is important that the APC-3K3A is provided so as to enable contact of APC-3K3A with skin cells as described herein at the site of tissue injury, as, while not wanting to be bound by hypothesis, it is believed that it is by this contact that the APC-3K3A provides for improvements in wound healing. Generally, those cells that have been contacted with APC-3K3A can be recognised by having the following characteristics: increased proliferation and decreased apoptosis; decreased caspase-3; activation of protease-activated receptors 1, 2 or 3; reduced NF-kB activation; reduced activation of signalling molecule, p38; reduced TNF secretion; increased matrix metalloproteinase (MMP)-2 protein and activation; reduced MMP-9; increased sphingoisine-1-phosphate; increased Angiopoietin (Ang)1 and decreased Ang 2; increased Tie2 activation; activation of signalling molecule Akt. Therefore, contact of cells with APC-3K3A, and therefore, therapeutic efficacy of treatment can be established by assessing for these cell phenotypes.

In one embodiment, a therapeutically effective amount of APC-3K3A may prevent or inhibit the formation of a pathologic scar in an individual. This outcome can be assessed by the qualitative or quantitative measures discussed below.

In certain embodiments, the therapeutically effective amount of APC-3K3A is from 0.1 µg to 5000 µg of APC-3K3A per $cm^2$ of the region of skin to which the APC-3K3A is applied, or from 1 µg to 2000 µg of APC-3K3A per $cm^2$ of the region of skin to which the APC-3K3A is applied, or from 10 µg to 1000 µg of APC-3K3A per $cm^2$ 2 of the region of skin to which the APC-3K3A is applied, or from 10 µg to 200 µg, or from 10 µg to 400 µg, or from 10 µg to 800 µg of APC-3K3A per $cm^2$ of the region of skin to which the APC-3K3A is applied The APC-3K3A may be administered once per week up to twice daily, depending on the nature of the tissue injury. It is generally provided for no more than 20 weeks of consecutive days, or from no more than 6 weeks of consecutive days.

Topical treatment methods, for example, using a paste, gel, cream, oil, lotion, foam, ointment or like substance are particularly useful where the relevant skin region is one that contains a ruptured skin surface, as this permits penetration of the APC-3K3A to the relevant strata of the skin tissue where the fibroblasts reside.

In one embodiment, the therapeutically effective amount of APC-3K3A may be from 0.1 to 2000 µg, preferably from 20 to 200 µg of APC-3K3A per $cm^2$ of the region of skin. A higher amount is generally preferred where the skin is more severely affected, or where the individual is at particular risk because of presence of local or systemic factors for impaired wound repair, as described above. Lower amounts may be preferred where the skin is not severely affected. The concentration of APC-3K3A in the formulation may be between about 10 µg/ml and 1 mg/ml and the volume of composition applied to the skin region is about 100 µg to 10 ml. In one embodiment, a formulation including APC-3K3A as the active component for wound healing or repair includes about 200 to 600 µg of APC-3K3A preferably about 200 to 250 µg of APC-3K3A, more preferably 250 µg of APC-3K3A or 500 µg of APC-3K3A. It is believed that this amount of APC-3K3A provides for acceleration of wound healing that is generally greater than that observed with APC alone, particularly where the wound area is less than 20 $cm^2$. Thus in another embodiment there is provided a method for the treatment of a dermal wound including the step of contacting a dermal wound with about 200 to 600 µg of APC-3K3A, preferably about 200 to 250 µg of APC-3K3A, more preferably 250 µg of APC-3K3A, or 500 µg of APC-3K3A, thereby treating the dermal wound. Where the wound area is greater than 20 cm² larger amounts of APC-3K3A are required, particularly from about 600 to 1000 µg of APC-3K3A, preferably about 800 to 1000 µg of APC-3K3A. Thus in another embodiment there is provided a method for the treatment of a dermal wound including the step of contacting a dermal wound with about 600 to 1000 µg of APC-3K3A, preferably about 800 to 1000 µg of APC-3K3A. In these embodiments, the formulation may be provided in a form suitable for topical or parenteral administration.

The composition may be provided to the skin generally with a sterile surface, such as a finger or spatula in a layer of no more than about 10 mm thickness, preferably about 3 mm thickness. It may then be rubbed or massaged into the skin region and surrounding area. The application is generally from once per day to once per week, and generally no longer than 20 weeks, or no longer than 12 weeks.

In one embodiment, the APC-3K3A containing composition may be applied to a solid substrate i.e. a bandage, dressing or the like, and the substrate then fixed to the relevant skin region.

In certain embodiments, the above outcomes are obtained by establishing a local concentration of APC-3K3A at least 2 times higher than basal line of APC. This amount of APC-3K3A and APC can be measured by measuring APC-3K3A and APC activity of skin biopsy using ELISA and chromogenic substrate Spectrozyme PCa assay as mentioned above. Intradermal or subcutaneous injection is generally preferred as an administration route when the stratum corneum is intact and of such nature that there is limited penetration of APC-3K3A across the skin layer. Generally a fine gauge needle on a (~28-34G) needle on a 0.3 to 1 ml syringe may be used. Multiple injections may be given to cover the surface area of the skin, with ~1 injection per cm². The amount per injection will vary from 10 µl to 1 ml, with typical amount being 50 µl. Generally the administration is given from once per day to once per week, and generally no longer than 20 weeks. Intradermal or sub cutaneous injection can be used concurrently with topical application of APC-3K3A.

APC-3K3A for use in a method or product described herein may be produced by a process as described in WO2005/007820. Further, APC-3K3A may be obtained from ZZ Biotech. The amino acid sequence of APC-3K3A is shown in FIG. 6.

In certain embodiments, APC-3K3A may incorporate modifications (eg amino acid substitutions, deletions, and additions of heterologous amino acid sequences), thereby forming APC-3K3A analogues which may, for example, enhance biological activity or expression of the respective protein. For example an APC-AK3A analogue may contain the RR229/230AA mutation corresponding to the calcium loop of APC, the RR306/312AA mutation corresponding to the autolysis loop of APC, or the RKRR306/314AAAA corresponding to the autolysis loop of APC. Each of these examples of APC analogues have reduced anticoagulant activity as compared with activity of native APC. However, each of them has related APC function in terms of binding to EPCR and PAR-1 or PAR-3.

APC-3K3A analogues generally have a sequence that is homologous to human protein C sequence. Percentage identity between a pair of sequences may be calculated by the algorithm implemented in the BESTFIT computer program (Smith & Waterman. J. Mol. Biol. 147:195-197, 1981; Pearson, Genomics 11: 635-650, 1991). Another algorithm that calculates sequence divergence has been adapted for rapid database searching and implemented in the BLAST computer program (Altschul et al., Nucl. Acids Res. 25:3389-3402, 1997). In comparison to the human sequence, the protein C polynucleotide or polypeptide may be only about 60% identical at the amino acid level, 70% or more identical, 80% or more identical, 90% or more identical, 95% or more identical, 97% or more identical, or greater than 99% identical.

Conservative amino acid substitutions (e.g., Glu/Asp, Val/Ile, Ser/Thr, Arg/Lys, Gln/Asn) may also be considered when making comparisons because the chemical similarity of these pairs of amino acid residues are expected to result in functional equivalency in many cases Amino acid substitutions that are expected to conserve the biological function of the polypeptide would conserve chemical attributes of the substituted amino acid residues such as hydrophobicity, hydrophilicity, side-chain charge, or size. In comparison to the human sequence, the protein C polypeptide may be only about 80% or more similar, 90% or more similar, 95% or more similar, 97% or more similar, 99% or more similar, or about 100% similar. Functional equivalency or conservation of biological function may be evaluated by methods for structural determination and bioassay.

The codons used may also be adapted for translation in a heterologous host by adopting the codon preferences of the host. This would accommodate the translational machinery of the heterologous host without a substantial change in chemical structure of the polypeptide.

APC-3K3A may also be glycosylated by methods well known in the art and which may comprise enzymatic and non-enzymatic means.

Suitable APC-3K3A mimetic compounds (ie compounds which mimic the function of APC-3K3A) may be designed using any of the methods well known in the art for designing mimetics of peptides based upon peptide sequences in the absence of secondary and tertiary structural information. For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity).

Alternatively, the mimetic compounds may be so-called peptoids (ie non-peptides) which include modification of the peptide backbone (ie by introducing amide bond surrogates by, for example, replacing the nitrogen atoms in the backbone with carbon atoms), or include N-substituted glycine residues, one or more D-amino acids (in place of L-amino acid(s)) and/or one or more α-amino acids (in place of β-amino acids or γ-amino acids). Further mimetic compound alternatives include "retro-inverso peptides" where the peptide bonds are reversed and D-amino acids assembled in reverse order to the order of the L-amino acids in the peptide sequence upon which they are based, and other non-peptide frameworks such as steroids, saccharides, benzazepinel,3,4-trisubstituted pyrrolidinone, pyridones and pyridopyrazines. Suitable mimetic compounds may also be designed/identified by structural modelling/determination, by screening of natural products, the production of phage display libraries, minimised proteins, SELEX (Aptamer) selection, combinatorial libraries and focussed combinatorial libraries, virtual screening/database searching, and rational drug design techniques well known in the art.

Suitable pharmaceutical compositions of APC-3K3A comprise APC-3K3A and a pharmaceutically-acceptable carrier. An APC-3K3A-containing composition may generally be one that is a stable lyophilized product of high purity comprising a bulking agent (such as sucrose, mannitol, trehalose, and raffinose), a salt (such as sodium chloride and potassium chloride), a buffer (such as sodium citrate, Tris-acetate, and sodium phosphate), and APC-3K3A. For example, a stable lyophilized composition may comprise a weight ratio of about 1 part APC-3K3A, between about 7-8 parts salt, and between about 5-7 parts bulking agent. An example of such a stable lyophilized composition is: 5.0 mg APC, 30 mg sucrose, 38 mg NaCl, and 7.56 mg citrate, pH 6.0, per vial.

The various recombinant and synthetic forms of APC-3K3A and APC-3K3A analogues can be tested for use in the treatment of a pathologic scar by screening for the relevant efficacy in an established animal model, examples of which are described below.

In one particularly preferred embodiment, the APC-3K3A is provided in the form of a composition or formulation that is adapted for topical administration to a relevant site of tissue injury, according to a method described herein. Examples of such formulations include those that can be applied directly to the relevant surface enabling local administration of the APC-3K3A to the relevant site. These formulations include gels, oils, sprays, roll on formulations, ointments, lotions, foams and the like. In one embodiment, the APC-3K3A is provided in the form of a methyl-cellulose gel and may contained stabilisers such as carbohydrates and salts.

Skin ointment may be a combination of organic, health, beauty or medicinal ingredients, usually in a petroleum oil base. This gives skin ointment a thicker, less water-soluble formula that stays on the surface of the body longer so that the ingredients can work more effectively to treat a wide variety of problems. There are many natural and organic skin ointments which can be ordered from companies (such as Therapex).

Clobetasol propionate (CP) foam (0.05%) may also be used. This is an emulsion aerosol foam that has been used for the treatment of inflammatory and pruritic manifestations of corticosteroid-responsive dermatoses in the United States and for inflammatory and pruritic manifestations of moderate to severe atopic dermatitis in Canada (Olux-E (clobetasol propionate) foam, 0.05% Stiefel Laboratories Inc, Research Triangle Park, NC (2011).

Where the formulation is a gel, it may contain APC-3K3A in an amount of 10-5000 µg/g gel.

An injectable formulation of APC-3K3A may be supplied as a sterile, lyophilized powder for intravenous infusion including APC-3K3A, sucrose, NaCl, and sodium citrate. The vials may be reconstituted with Sterile Water for Injection, USP, to give a concentration of about 2 mg/ml APC-3K3A, and this diluted APC-3K3A may then be added to 0.9% Sodium Chloride Injection to give a concentration of from about 100 to about 500 µg/ml APC-3K3A for administration to a patient. This is a particularly preferred formulation for administration of APC-3K3A by subcutaneous injection.

EXAMPLES

Example 1 APC-3K3A Promotes Wound Repair in an In Vivo Excisional Model

Materials & Methods

C57BL/6J mice were at 7-8 weeks of age when starting wounding protocol. Mice were obtained from and housed at Kearns Facility, Kolling Medical Research Institute, under a 12 h light/12 h dark cycle at 22° C.

Full-thickness skin wounds were made using an iris scissor and a sterile 6-mm punch biopsy tool was used to outline a pattern on the dorsum of the mice.

Recombinant (r)3K3A-APC, rAPC or phosphate buffered saline (PBS) control was injected into the skin at 4 points, each receiving 10 µl, around the internal periphery of the wounds, and 10 µl added topically to the wound, once a day for the first three consecutive days.

The animals were then kept under anaesthesia for 15 minutes to allow absorption of the solution. The wounds were left open and the animals were housed in individual cages.

Wound healing was monitored by taking digital photographs and blindly measuring the wound area by tracing the wound perimeter with a thin tipped marker onto sterile Visitrak Grid 6. Tracings were then scanned to obtain a digital reading of the wound area.

All procedures were performed according to the guidelines of the local animal care and ethics committee.

Results & Discussion

Figure 2:
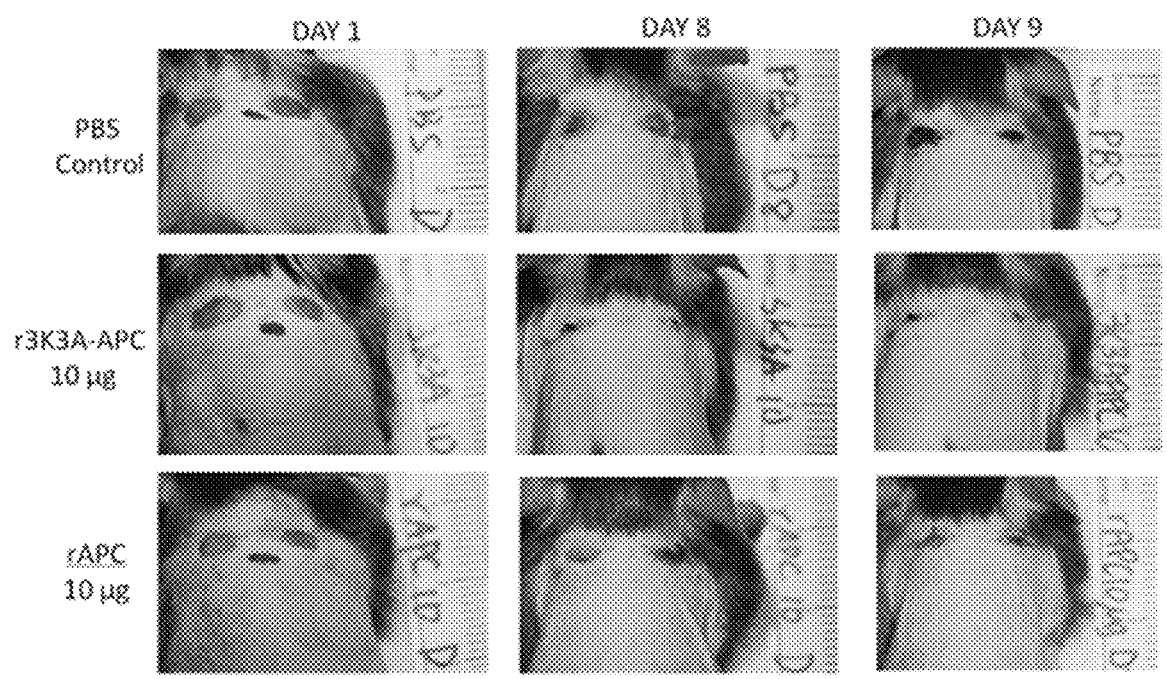
FIG. 2 Improvements in wound repair in APC and APC-3K3A treated mice.

FIG. 1 and FIG. 2: results are shown as mean±SE. For PBS, 10 µg r3K3A-APC and 10 µg rAPC: number of wounds=12, number of mice=6. For other concentrations: wounds=6, mice=3. $P<0.01$, PBS vs r3K3A-APC 10 µg. $P<0.01$, r3K3A-APC 10 µg vs rAPC 10 µg (Repeated measures ANOVA). In summary, the optimal dose in this study for rAPC-3K3A is 10 µg. The data shows that rAPC-3K3A enhances wound healing compared to PBS control. Further, rAPC-3K3A enhances wound healing compared to rAPC.

There was a significant difference between 10 µg 3K3A and PBS at early timepoints, with $p<0.01$ on days 2, 3 and 4. Similar differences were seen between 10 µg APC and 10 µg 3K3A. The % improvement of 10 µg 3K3A over PBS was, 28%, 23% and 30% on days 2, 3 and 4 respectively. The % improvement of 10 µg 3K3A over 10 µg APC was 24%, 29% and 36% on days 2, 3 and 4 respectively. The faster a wound heals, especially at early stages, the greater the likelihood of tissue regeneration occurring, rather than just repair. Regeneration usually refers to new tissue that is the same as the original tissue whereas repair is associated with scarring (Min, Su; Wang, Song W; Orr, William (2006). "*Graphic general pathology: 2.2 complete regeneration:*". Pathology. pathol.med.stu.edu.cn. Retrieved 2012-12-07). The first few days is the critical time period for regeneration during wound healing—the slower the healing, the more likelihood that scarring will occur (Ferguson MW1, O'Kane S; Philos Trans R Soc Lond B Biol Sci. 2004 May 29; 359(1445):839-50. Scar-free healing: from embryonic mechanisms to adult therapeutic intervention). (Profyris C, Tziotzios C and Do Vale I. Cutaneous scarring: Pathophysiology, molecular mechanisms, and scar reduction therapeutics Part I. The molecular basis of scar formation. J Am Acad Dermatol 2012; 66: 1-10). Thus, the marked improvement induced by 10 µg 3K3A at early timepoints more likely leads to the desired scarless healing, compared to treatment with 10 µg APC or PBS. This early thrust provides momentum for accelerated angiogenesis, granulation tissue formation, epithelialization and matrix reorganisation. This provides a tangible advantage over normal healing (Control) and treatment with 10 μg APC.

Treatment with 30 μg 3K3A displayed slower healing than 10 μg 3K3A. This type of response is not uncommon in biological drug studies. One explanation is that the 3K3A receptors become saturated and a signalling feedback mechanism occurs, where intracellular messengers send biochemical signals to inhibit the action of 3K3A possibly by affecting its receptors. Precedent for this effect is seen by APC's effects on keratinocyte migration and wound closure in vitro (Xue M, Thompson P, Kelso I, Jackson C. Exp Cell Res. 2004 Sep. 10; 299(1):119-27. Activated protein C stimulates proliferation, migration and wound closure, inhibits apoptosis and upregulates MMP-2 activity in cultured human keratinocytes.) Such a feedback mechanism was not observed for APC, as 30 μg APC had a greater effect than 10 μg APC (p<0.01). These data suggest that APC at 10 μg is yet to reach its peak whereas 10 μg 3K3A has peaked, implying that 3K3A is more potent than APC as a therapeutic drug for wound healing. Overall, the data above show that 3K3A is different from and has a clear advantage over APC.

Figure 3:
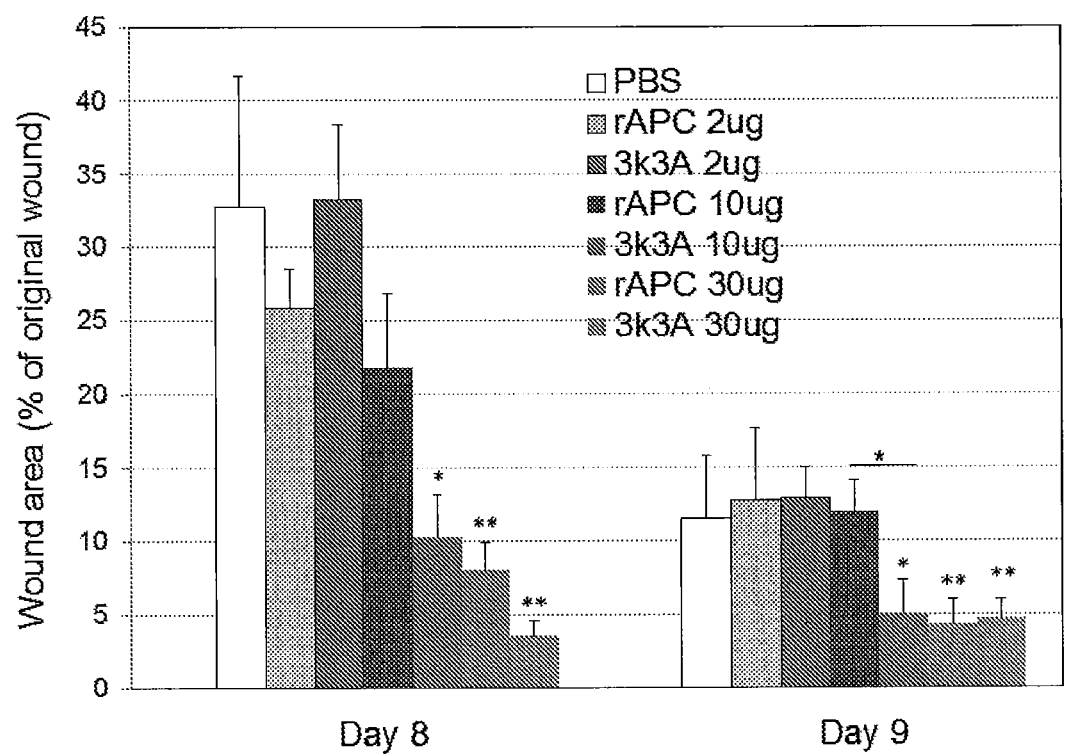
FIG. 3. APC-3K3A has a greater potency for decreasing wound area than APC.

FIG. 3: *P<0.05, ** P<0.01, when compared to control (ANOVA, Bnferonni's). On Days 8 and 9, r3K3A-APC at both 10 and 30 μg enhanced wound healing whereas for rAPC only the higher concentration, 30 μg, was effective. On day 9, there was a significant difference between 10 μg r3K3A-APC and 10 μg rAPC.

Figure 4:
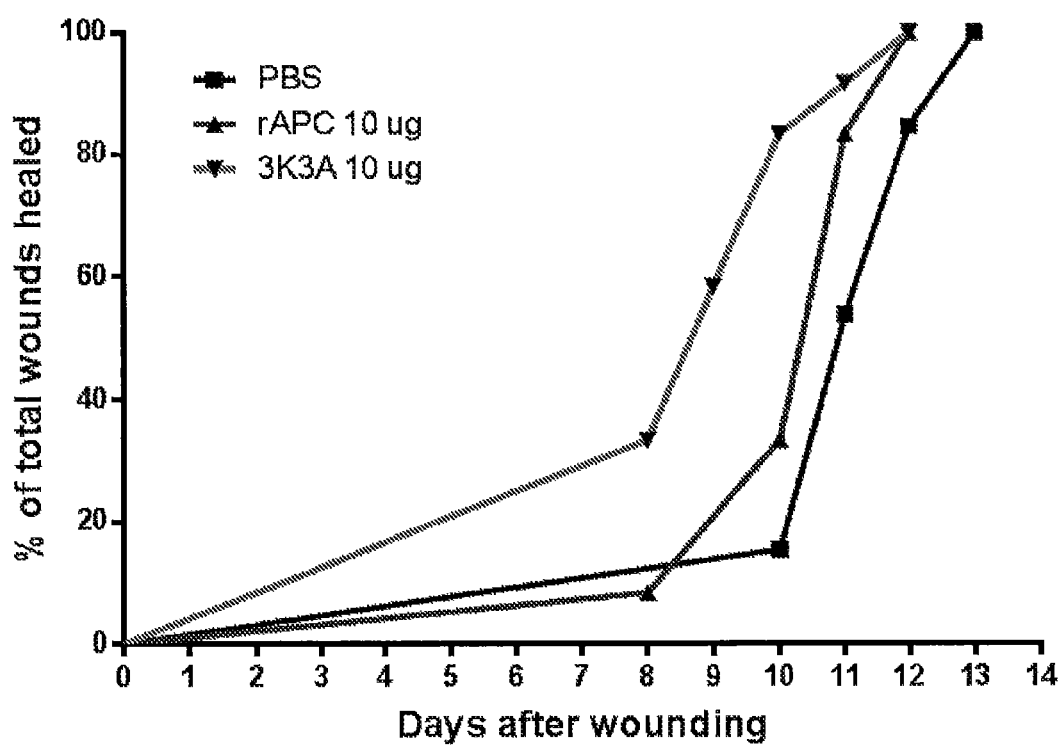
FIG. 4. APC-3K3A increases rate of wound healing compared with APC.

FIG. 4: P<0.01, between 3K3A-APC (n=12) 10 μg Vs PBS (n=12). P<0.05, between 3K3A-APC10 μg (n=12) Vs rAPC10 μg (n=12). No difference between rAPC 10 μg and PBS (p=0.064) (Using Kaplan-Meier and log rank analysis). In summary, at 10 μg 3K3A-APC completely heals wounds faster than placebo or rAPC (10 μg).

Figure 5:
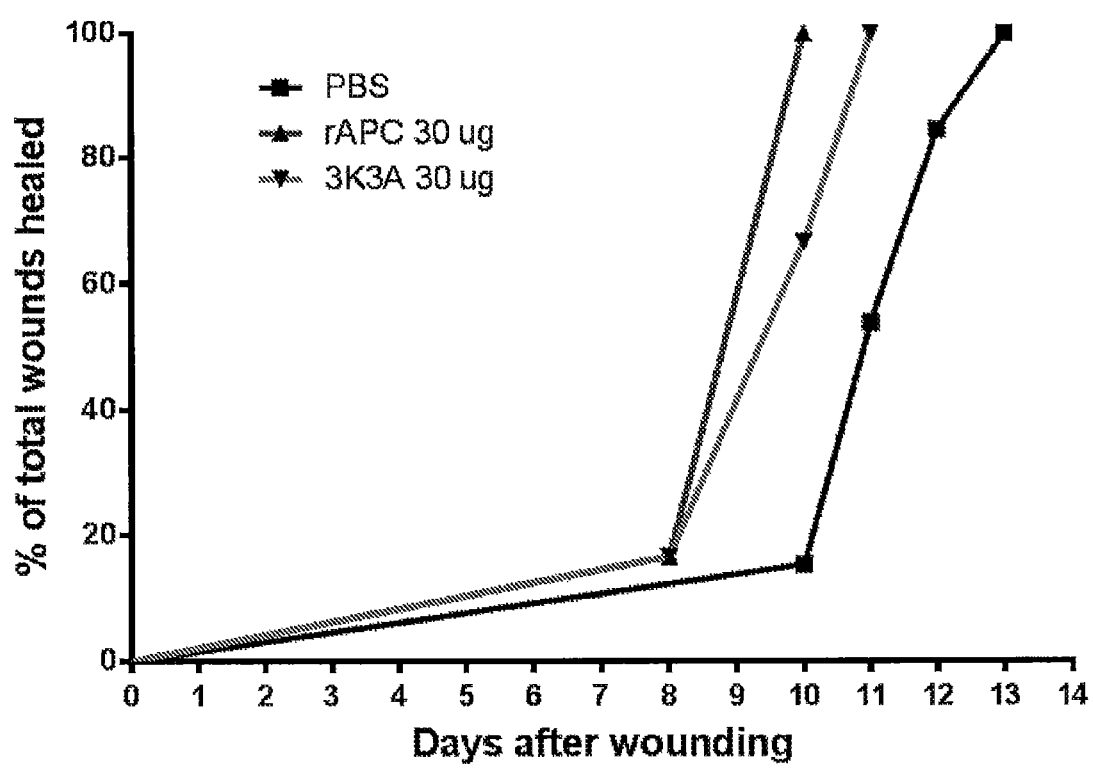
FIG. 5. APC-3K3A and APC increase rate of wound healing compared with placebo.

FIG. 5: P<0.05, between rAPC 30 μg (n=6) Vs PBS (n=12). P<0.05, between 3k3A-APC 30 μg (n=6) Vs PBS (n=12). No difference between rAPC 30 μg and 3k3A APC 30 μg. (Using Kaplan-Meier and log rank analysis). In summary, at 30 μg, 3K3A-APC and rAPC both completely heal wounds faster than placebo.

The invention claimed is:

1. A method for accelerating healing of a dermal wound including the step of directly contacting a dermal wound with an effective amount of 3K3A-APC, thereby accelerating the healing of the dermal wound.

2. The method of claim 1, further comprising the step of topically administering the 3K3A-APC to the wound, thereby contacting the dermal wound with the effective amount of 3K3A-APC.

3. The method of claim 2, wherein 3K3A-APC is topically administered to the wound in the form of a formulation selected from the group consisting of a gel, an ointment, a lotion and a spray.

4. The method of claim 1, wherein the 3K3A-APC is administered to the wound by intradermal injection, thereby contacting the wound with an effective amount of 3K3A-APC.

5. The method of claim 1, wherein the dermal wound is not characterised by significant apoptosis, or otherwise does not arise from apoptosis.

6. The method of claim 2, wherein the dermal wound is not characterised by significant apoptosis, or otherwise does not arise from apoptosis.

7. The method of claim 4, wherein the dermal wound is not characterised by significant apoptosis, or otherwise does not arise from apoptosis.

8. The method of claim 2, wherein the dermal wound is a chronic dermal wound.

9. The method of claim 4, wherein the dermal wound is a chronic dermal wound.

10. The method of claim 2, wherein the dermal wound is an acute dermal wound.

11. The method of claim 4, wherein the dermal wound is an acute dermal wound.

12. The method of claim 2, wherein the wound is a burn, incision, laceration, abrasion, puncture or ulcer.

13. The method of claim 4, wherein the wound is a burn, incision, laceration, abrasion, puncture or ulcer.

14. The method of claim 2, wherein the 3K3A-APC is provided in an amount of 250 μg or 500 μg.

15. The method of claim 4, wherein the 3K3A-APC is provided in an amount of 250 μg or 500 μg.

16. The method of claim 2, wherein 3K3A-APC concentration at the dermal wound is at least 2 times higher than APC basal level.

17. The method of claim 4, wherein 3K3A-APC concentration at the dermal wound is at least 2 times higher than APC basal level.

* * * * *

UNITED STATES PATENT AND TRADEMARK OFFICE
CERTIFICATE OF CORRECTION

| | |
|---|---|
| PATENT NO. | : 12,214,024 B2 |
| APPLICATION NO. | : 16/569975 |
| DATED | : February 4, 2025 |
| INVENTOR(S) | : Xue et al. |

It is certified that error appears in the above-identified patent and that said Letters Patent is hereby corrected as shown below:

On the Title Page

Item (56) References Cited, OTHER PUBLICATIONS, Page 3, Column 1, Occleston et al. cite, Line 24: Please correct "(TGFB3)" to read --(TGFβ3)--

In the Specification

Column 10, Line 41: Please correct "10 µg" to read --10 ug--

Column 10, Line 43: Please correct "10 µg" to read --10 ug--

Column 10, Lines 43-44: Please correct "10 µg" to read --10 ug--

Column 10, Line 44: Please correct "10 µg" to read --10 ug--

Column 10, Line 46: Please correct "10 µg" to read --10 ug--

Column 10, Line 65: Please correct "10 µg" to read --10 ug--

Column 10, Line 67: Please correct "10 µg" to read --10 ug--

Column 11, Line 4: Please correct "10 µg" to read --10 ug--

Column 11, Line 5: Please correct "30 µg" to read --30 ug--

Column 11, Line 6: Please correct "10 µg" to read --10 ug--

Column 11, Line 18: Please correct "30 µg" to read --30 ug--

Signed and Sealed this
Fifteenth Day of July, 2025

Coke Morgan Stewart
*Acting Director of the United States Patent and Trademark Office*

Column 11, Line 19: Please correct "10 μg" to read --10 ug--

Column 11, Lines 19-20: Please correct "10 μg" to read --10 ug--

Column 11, Line 20: Please correct "10 μg" to read --10 ug--

SEQUENCE LISTING

```
<160> NUMBER OF SEQ ID NOS: 1

<210> SEQ ID NO 1
<211> LENGTH: 419
<212> TYPE: PRT
<213> ORGANISM: Artificial Sequence
<220> FEATURE:
<223> OTHER INFORMATION: APC-3K3A

<400> SEQUENCE: 1

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
```

-continued

```
            210                 215                 220
Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro
```